(12) United States Patent
Lund et al.

(10) Patent No.: US 11,584,947 B2
(45) Date of Patent: Feb. 21, 2023

(54) METHOD FOR THE RAPID DETECTION OF BACTERIAL SPORES IN AN INDUSTRIAL PROCESS

(71) Applicant: ECOLAB USA INC., St. Paul, MN (US)

(72) Inventors: Liliya Lund, Des Plaines, IL (US); Laura Rice, St. Charles, IL (US)

(73) Assignee: ECOLAB USA INC., St. Paul, MN (US)

( * ) Notice: Subject to any disclaimer, the term of this patent is extended or adjusted under 35 U.S.C. 154(b) by 62 days.

(21) Appl. No.: 16/629,892

(22) PCT Filed: Jul. 12, 2017

(86) PCT No.: PCT/US2017/041736
§ 371 (c)(1),
(2) Date: Jan. 9, 2020

(87) PCT Pub. No.: WO2019/013781
PCT Pub. Date: Jan. 17, 2019

(65) Prior Publication Data
US 2020/0239928 A1 Jul. 30, 2020

(51) Int. Cl.
*C12Q 1/04* (2006.01)
*C12Q 1/66* (2006.01)
*G01N 21/76* (2006.01)

(52) U.S. Cl.
CPC ............... *C12Q 1/04* (2013.01); *C12Q 1/66* (2013.01); *G01N 21/76* (2013.01)

(58) Field of Classification Search
None
See application file for complete search history.

(56) References Cited

U.S. PATENT DOCUMENTS

| | | | |
|---|---|---|---|
| 3,933,592 | A | 1/1976 | Clendenning |
| 5,648,232 | A | 7/1997 | Squirrell |
| 5,918,259 | A | 6/1999 | Squirrell |
| 6,703,211 | B1 | 3/2004 | Shultz et al. |
| 7,183,048 | B2 | 2/2007 | Felkner et al. |
| 8,613,837 | B2 | 12/2013 | Rice et al. |
| 9,290,789 | B2 | 3/2016 | Okanojo et al. |
| 11,421,260 | B2 | 8/2022 | Tu et al. |
| 2008/0014607 | A1 | 1/2008 | Champiat |
| 2012/0231961 | A1 | 9/2012 | La Duc et al. |
| 2013/0189152 | A1 | 7/2013 | Rice et al. |
| 2014/0141443 | A1 | 5/2014 | Rice et al. |
| 2015/0305344 | A1 | 10/2015 | Burke et al. |
| 2015/0322476 | A1 | 11/2015 | Sellappan et al. |

FOREIGN PATENT DOCUMENTS

| | | |
|---|---|---|
| JP | 7-239318 A | 9/1995 |
| JP | 2001-238691 A | 9/2001 |
| JP | 2003-325152 A | 11/2003 |
| JP | 2005-504239 A | 1/2005 |
| JP | 2005-110638 A | 4/2005 |
| JP | 2012-196181 A | 10/2012 |
| JP | 2013-27379 A | 2/2013 |
| WO | 2004/027020 A2 | 4/2004 |
| WO | 2005/033329 A2 | 4/2005 |
| WO | 2005/093085 A1 | 10/2005 |
| WO | 2013/177229 A1 | 11/2013 |
| WO | 2014/015044 A1 | 1/2014 |

OTHER PUBLICATIONS

Ratphitagsanti, Wannasawat; et al; "High-throughput detection of spore contamination in food packages and food powders using tiered approach of ATP bioluminescence and real-time PCR" LWT—Food Science and Technology, 46, 341-348, 2012 (Year: 2012).*
Passman, Frederick J; et al; "Adenosine Triphosphate Testing" LASH 2013, The 13th International Conference on Stability, Handling and Use of Liquid Fuels, Rhodes, Greece, Oct. 6-10, 2013 (Year: 2013).*
Hoefel, Daniel; et al; "A comparative study of carboxyfluorescein diacetate and carboxyfluorescein diacetate succinimidyl ester as indicators of bacterial activity" Journal of Microbiological Methods, 52, 379-388, 2003 (Year: 2003).*
Veciana-Nogues, MT; et al; "Determination of ATP related compounds in fresh and canned tuna fish by HPLC" Food Chemistry, 59, 467-472, 1997 (Year: 1997).*
Abehlo, M., "Extraction and Quantification of ATP as a Measure of Microbial Biomass: Chapter 30", Methods to Study Litter Decomposition: A Practical Guide, Springer, 223-230 (2005).
Halvorson, H. et al., "Dormancy of Bacerial Endospores: Regulatio of Electron Transport by Dipicolinic Acid", Proc. N.A.S., 1171-1180 (1958).
Leggett, M.J. et al., "Bacterial spore structures and their protective role in biocide resistance", Journal of Applied Microbiology, 113: 485-498 (2012).
Lundin, A. et al., "Comparison of Methods for Extraction of Bacterial Adenine Nucleotides Determined by Firefly Assay", Applied Microbiology, 30(5): 713-721 (1975).
Omidbakhsh, N. et al., "How Reliable are ATP Bioluminescence Meters in Assessing Decontamination of Environmental Surfaces in Healthcare Settings", PLOS One, 9(6): 1-8 (Jun. 2014).
Setlow, P. et al., "Biochemical Studies of Bacterial Sporulation and Germination", The Journal of Biological Chemistry, 245(14): 3637-3644 (Jul. 1970).
Setlow, P. et al., "Biochemical Studies of Bacterial Sporulation and Germination", The Journal of Biological Chemistry, 245(14): 3645-3652 (Jul. 1970).
Chinese First Office Action for Application No. 201780092989.5 dated Apr. 8, 2021 (Chinese and English Translation).

(Continued)

*Primary Examiner* — David W Berke-Schlessel
(74) *Attorney, Agent, or Firm* — Merchant & Gould P.C.

(57) ABSTRACT

A method for detecting the presence of bacterial spores is described by measuring microbial metabolic activity over time. Spores are distinguished from vegetative cells and other microorganisms by detecting a burst of metabolic activity indicating germination of spores. This method may be used to detect bacterial spores in a commercial process system, such as a papermaking system within the time frame of a typical work shift.

21 Claims, 5 Drawing Sheets

(56) References Cited

OTHER PUBLICATIONS

International Search Report and Written Opinion of the International Searching Authority for International Patent Application No. PCT/US2017/041736 dated Nov. 8, 2017, 17 pages.
Fujinami, Y. et al., "Sensitive Detection of Bacteria and Spores Using a Portable Bioluminescence ATP Measurement Assay System Distinguishing from White Powder Materials", Journal of Health Science, 50(2): 126-132 (Jan. 2004).
Chollet, R. et al., "Use of ATP Bioluminescence for Rapid Detection and Enumeration of Contaminants: The Milliflex Rapid Microbiology Detection and Enumeration System", Bioluminescence—Recent Advances in Oceanic Measurements and Laboratory Applications, 99-118 (Feb. 2012).
Russell, A.D., "Bacterial Spores and Chemical Sporicidal Agents", Clinical Microbiology Reviews, 99-119 (Apr. 1990).
Walsh, S. et al., "An assessment of the metabolic activity of starved and vegetative bacteria using two redox dyes", Journal of Microbiological Methods, 24:1-9 (Jan. 1995).
Robertson et al., "Diagnosis of Microbial Problems on Paper Machines," Japan Tappi Journal, vol. 57, No. 6, pp. 830-836 (2003) (with partial English translation).
Tsukatani, "Develoment of a Microbial Detection Method Using the Water-soluble Tetrazolium Salt WST: Food Industry Applications," Nippon Shokuhin Kagaku Kogyo, vol. 62, No. 7, pp. 321-327 (2015).
Brookes et al., "The Adenylate Energy Charge of the Soil Microbial Biomass," Soil Biol. Biochem., vol. 15, No. 1, pp. 9-16 (1983).
Fajardo-Cavazos et al., "Persistence of Biomarker ATP and ATP-Generating Capability in Bacterial Cells and Spores Contaminating Spacecraft Materials under Earth Conditions and in a Simulated Martian Environment," Applied and Environmental Microbiology, pp. 5159-5167 (Aug. 2008).
Lee et al., "A rapid screening method for the detection of viable spores in powder using bioluminescence," Luminescence, vol. 19, pp. 2019-211 (2004).
Min et al., "Simple and Rapid Method for Detection of Bacterial Spores in Powder Useful for First Responders," J Environ Health. Apr. 2006:68(8):34-7, 44, 46 (Abstract Only).
Wuytack et al., "Comparative Study of Pressure-Induced Germination of Bacillus subtilis Spores at Low and High Pressures," Applied and Environmental Microbiology, vol. 64, No. 9, pp. 3220-3224 (Sep. 1998).

\* cited by examiner

US 11,584,947 B2

METHOD FOR THE RAPID DETECTION OF BACTERIAL SPORES IN AN INDUSTRIAL PROCESS

CROSS REFERENCE TO RELATED APPLICATIONS

This application is a National Stage Application of PCT/US2017/041736, filed on Jul. 12, 2017, which is incorporated in this application by reference. To the extent appropriate, a claim of priority is made to the above disclosed application.

BACKGROUND

Endospores are dormant, tough, non-reproductive structures produced by particular species of bacteria in the Firmicute phylum. Endospores, or spores, are produced when bacterial cells in their vegetative state are exposed to stress or lack of nutrients. Endospores have a very low metabolic rate and therefore cannot be detected by methods typically employed to rapidly detect vegetative bacterial cells. Further, spores are extremely difficult to kill because they evolved to survive harsh conditions such as UV, heat, disinfectants, desiccation, and starvation. Upon exposure to favorable conditions and nutrients, the spores germinate to produce vegetative cells.

Spore-producing bacteria are problematic because they cause illness in humans and animals, spoilage in food and beverages, and promote the perpetuation of biofilm. Spore-producing bacterial strains that are of particular concern are those in the *Bacillus* and *Clostridium* genera. Both are gram-positive, rod-shaped bacteria that include species that are harmful to humans. *B. anthracis* produces anthrax toxin and *B. cereus* causes food poisoning. *C. botulinum* causes botulism (also known as Botox), *C. difficile* causes diarrhea, *C. perfringens* causes food poisoning, and *C. tetani* causes tetanus. *Bacillus cereus* is one of the most problematic bacteria because it has been identified as possessing increased resistance to germicidal chemicals used to decontaminate environmental surfaces.

*Bacillus cereus* is frequently diagnosed as a cause of gastrointestinal disorders and has been suggested to be the cause of several food-borne illness outbreaks. Due to its rapid sporulating capacity, *B. cereus* easily survives in the environment. This bacterium can contaminate food directly and indirectly. *B. cereus* can contaminate raw milk directly via feces and soil, and can survive intestinal passage in cows and the pasteurization process. Indirect contamination can come from the presence of *B. cereus* spores in liquid and food packaging. Spores present in materials that come into direct contact with food can cause migration of spores into the food, resulting in spoilage.

Given the negative implications of these bacteria being ingested by humans, government agencies have set standards or guidelines intended to reduce the presence of spores. Current spore detection methods require 48 hours to complete. The most common way to test for bacterial spores is a plating technique. This two-day delay is impractical for many industries. In the case of product testing, a two-day delay requires an extraordinary amount of product to be quarantined until the testing results are complete. This is a problem, for example, in the paper or paperboard industry.

Likewise, when testing food and beverage processing equipment, the equipment is only taken down for cleaning periodically and, as a practical matter, cannot remain offline for two days. Hospitals cannot keep hospital rooms empty for two days while waiting for test results designed to identify the presence of spores on surfaces in a hospital room after a patient that has been infected with *C. diff* has been discharged. And it is not practical to hold quantities of food or water under quarantine, especially where the food may spoil while waiting or where the water or fluid continually changes (e.g., cooling tower water, beverages, milk during milk processing).

It is against this background that the present disclosure is made.

SUMMARY

In general terms, this disclosure is directed to methods of rapidly detecting and distinguishing bacterial spores from vegetative cells.

In one aspect, a method of detecting and differentiating bacterial spores from vegetative cells and other microorganisms in a sample is provided. A sample is prepared to be tested for the presence of bacterial spores. A baseline level of microbial metabolic activity in the sample is measured. The sample is incubated in conditions to initiate germination and subsequent levels of microbial metabolic activity are monitored in the sample. After about 5 to about 8 hours of incubation, the presence or absence of a burst of microbial metabolic activity in the sample is detected.

In some aspects, the method of detecting and differentiating bacterial spores from vegetative cells and other microorganisms in a sample includes additional steps. In some embodiments, preparing the sample includes collecting a sample containing an unknown quantity of spores, vegetative cells, or both spores and vegetative cells. The sample is disintegrated and placed in a dish or container.

In some aspects, the sample is collected from a hard surface, a liquid, a slurry (starch, carbonate, clay, or $TiO_2$), or a paper product. In some embodiments, the sample is collected from a hard surface such as food and beverage processing equipment, pipes, tanks, evaporators, spray nozzles, dairy processing equipment, milk tanks, milk trucks, milking equipment, countertops, cooking surfaces, bathroom surfaces such as sinks and toilet handles, light switch panels, doorknobs, call buttons, phone handles, remote controls, desktops, patient rails, grab bars, surgical instruments, equipment inside paper mills including pipes, chests, headboxes, broke towers, saveall blades, and forming wire. In other embodiments, the sample is taken from a liquid such as process waters, incoming water, cooling tower water, treated and untreated wastewater, paper furnish, thin and tick stock, white water, uhle box water, tray water, fruit and vegetable flume water, protein process water, hydroponic waters or seafood farming water, and water for agricultural uses. In yet other embodiments, the sample is taken from a paper product such as finished paper products and finished board products both for food contact and non-food contact grades; drapes for surgical or medical use; aseptic packaging containers; plastic food and beverage containers; food cans; aluminum and PET beverage containers; bags, films, and modified atmosphere packaging.

In some embodiments, vegetative cells in the sample are inactivated. In such embodiments, the vegetative cells can be inactivated by heating the sample for about 5 to 15 minutes at a temperature of about 80° C. to about 110° C.

In some embodiments, the microbial metabolic activity is determined by measuring adenosine triphosphate (ATP). In such embodiments, ATP can be measured by adding luciferase and luciferin to the sample and measuring light emissions in relative light units (RLUs). ATP can also be measured by HPLC. In other embodiments, the microbial metabolic activity is detected by metabolic dyes.

In some embodiments, incubating the sample involves providing a nutrient broth and a germination enhancer to the sample. A biocide neutralizing agent is optionally added. The sample is incubated at a temperature of about 30° C. to about 45° C. In some aspects, the nutrient broth is 2× nutrient broth and the germination enhancer is L-alanine.

In some aspects, monitoring the sample for microbial metabolic activity is done by adding luciferase and luciferin to the sample and measuring light emissions at multiple points of time during an 8-hour period of incubation. In some embodiments, the measuring occurs every hour.

In some aspects, detecting a burst of microbial metabolic activity occurs when at least 10 times higher microbial metabolic activity is measured in the sample after incubation compared to the initial measurement of the sample. Detection of this burst results in a determination that spores are present in the sample. In some embodiments, the method can determine the presence or absence of bacterial spores in the sample within 8 hours of preparing the sample, and spores are differentiated from vegetative cells.

In some aspects, the method further includes selecting an antimicrobial treatment based upon the presence or absence of spores, vegetative cells, or both spores and vegetative cells. In such aspects, the antimicrobial treatment can be selected from the group consisting of chlorine dioxide, ozone, glutaraldehyde, sodium hypochlorite, peracid, UV, extreme heat, and radiation when spores are detected. When only vegetative cells are detected, the antimicrobial treatment is selected from the group consisting of: isothiazolin; glutaraldehyde; dibromonitrilopropionamide; carbamate; quaternary ammonium compounds; sodium hypochlorite; chlorine dioxide; peracetic acid; ozone; chloramines; bromo-sulfamate; bromo-chloro-dimethyl hydantoin; dichloro-dimethyl hydantoin; monochloramine; sodium hypochlorite used in combination with ammonium salts and stabilizers including dimethyl hydantoin amino acids, cyanuric acid, succinimide, urea; and a combination. In some embodiments, the method further includes applying the selected antimicrobial treatment to the hard surface, liquid, or paper product.

In one embodiment, a method of detecting and differentiating bacterial spores from vegetative cells and other microorganisms begins by taking a sample having an unknown quantity of vegetative cells and spores from a hard surface, a liquid, or a paper product. The sample can be taken from a hard surface such as food and beverage processing equipment, pipes, tanks, evaporators, spray nozzles, dairy processing equipment, milk tanks, milk trucks, milking equipment, countertops, cooking surfaces, bathroom surfaces such as sinks and toilet handles, light switch panels, doorknobs, call buttons, phone handles, remote controls, desktops, patient rails, grab bars, surgical instruments, equipment inside paper mills including pipes, chests, headboxes, broke towers, saveall blades, and forming wire. The sample may also be taken from a liquid such as process waters, incoming water, cooling tower water, treated and untreated wastewater, paper furnish, thin and tick stock, white water, uhle box water, tray water, fruit and vegetable flume water, protein process water, hydroponic waters or seafood farming water, and water for agricultural uses. And the sample may be taken from a paper product such as finished paper products and finished board products both for food contact and non-food contact grades; drapes for surgical or medical use; aseptic packaging containers; plastic food and beverage containers; food cans; aluminum and PET beverage containers; bags, films, and modified atmosphere packaging. Vegetative cells in the sample are inactivated by heating the sample for about 5-15 minutes, 7-13 minutes, or 9-11 minutes at a temperature of about 80° C. to about 110° C., about 85° C. to about 105° C. or about 90° C. to about 100° C. A baseline level of metabolic activity is determined by measuring ATP levels in the sample. The ATP levels are measured by adding luciferase and luciferin to the sample and measuring light emissions in RLUs. The sample is incubated at a temperature of about 30° C. to about 45° C. with 2× nutrient broth and an L-alanine germination enhancer to initiate germination. The sample is monitored microbial metabolic activity by adding luciferase and luciferin to the sample and measuring light emissions at multiple points of time during an 8-hour period of incubation. After about 5 to about 8 hours of incubation, the presence of a burst of microbial metabolic activity of at least 10 times higher than the baseline level indicates the presence of spores. The absence of a burst of microbial metabolic activity indicates the absence of spores. If spores are detected, an antimicrobial treatment is selected to treat the spores and is applied to the hard surface, liquid, or paper product. If spores are not detected, an antimicrobial treatment is selected to treat vegetative cells and is applied to the hard surface, liquid, or paper product.

DETAILED DESCRIPTION

Figure 1:
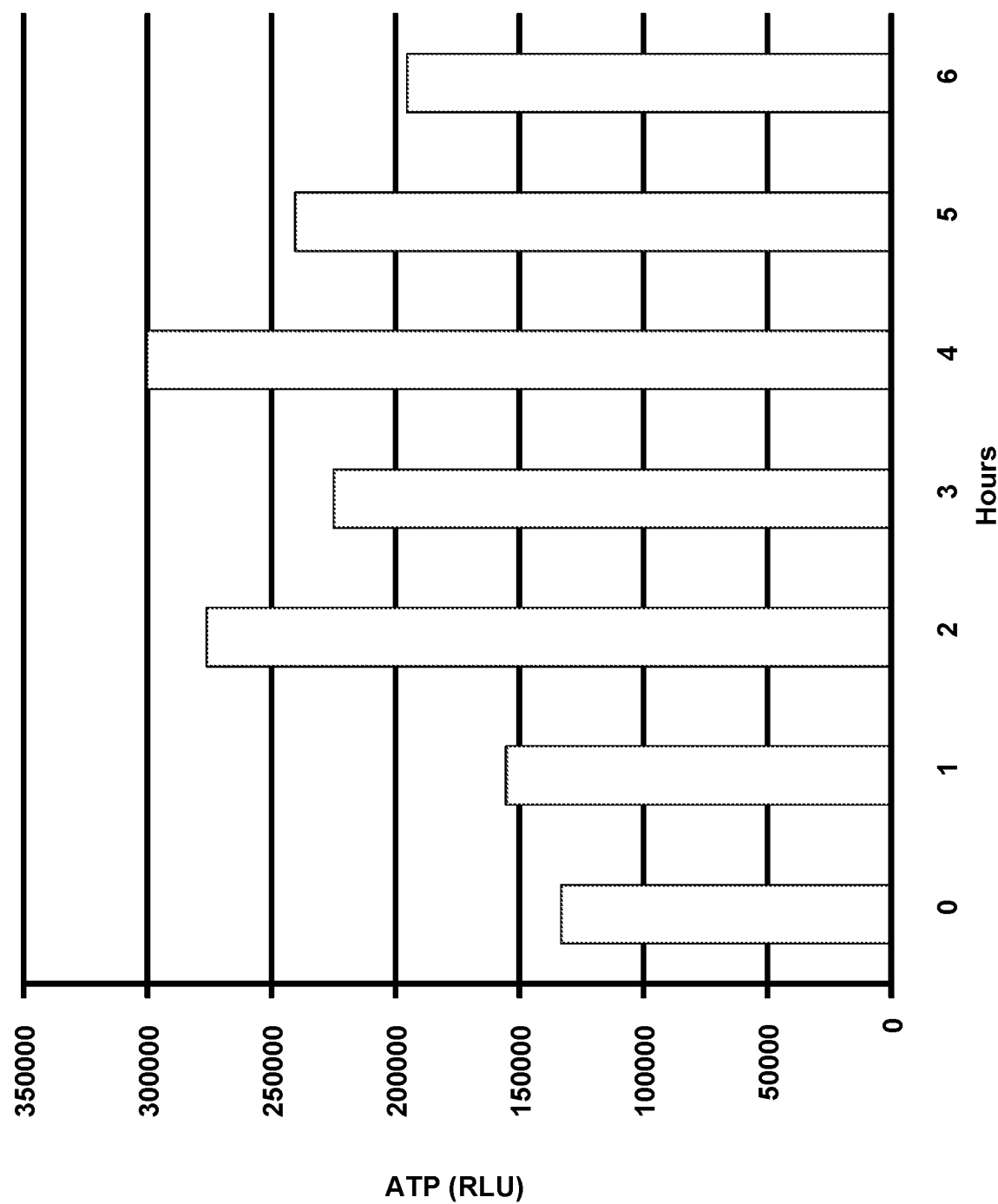
FIG. 1 is a chart of ATP production over time in an industrial water sample without heat treatment, without germination enhancer, and without nutrients.

The present disclosure is directed to methods of detecting bacterial spores. In particular, embodiments are directed to a method of rapidly distinguishing the presence of bacterial spores from the presence of other microorganisms and determining the source of a spore contamination. Furthermore, the present disclosure distinguishes between vegetative and spore states of spore-forming bacteria.

The following definitions are provided to determine how terms used in this application, and in particular how the claims, are to be construed. The organization of the definitions is for convenience only and is not intended to limit any of the definitions to any particular category.

The term "bacterial spores" or "endospores" as used herein, refers to structures produced by some species of bacteria, such as *Bacillus* and *Clostridium* species. Spores enable bacteria to remain dormant in harsh conditions such as extreme temperatures, drought, and chemical treatments.

The term "germination," as used herein, refers to the growth of vegetative cells from dormant bacterial spores. Germination takes place when spores are exposed to favorable conditions for vegetative cells to grow.

The term "vegetative bacterial cells," as used herein, refers to bacterial cells that are actively growing, exhibiting metabolic activity, and dividing.

The term "biocide" as used herein, refers to a chemical substance or microorganism intended to destroy or neutralize any harmful microorganism by chemical or biological means. Biocides may include preservatives, insecticides, disinfectants, and pesticides that are used to control organisms that are harmful to human or animal health or cause damage to natural or manufactured products.

The term "sporicide" as used herein, refers to a physical or chemical agent or process having the ability to cause greater than a 90% reduction (1-log order reduction) in the population of spores of *Bacillus cereus* or *Bacillus subtilis*. Preferably, the sporicidal compositions of the disclosure provide greater than a 99% reduction (2-log order reduction), more preferably greater than a 99.99% reduction (4-log order reduction), and most preferably greater than a 99.999% reduction (5-log order reduction) in such population.

The term "quarantine" refers to separation and isolation of objects that may or may not be contaminated or infected with microorganisms.

The term "rapid detection" as used herein, refers to methods of detecting bacteria and bacterial spores in less than 48 hours. Preferably, "rapid detection" refers to detecting bacteria in less than 24 hours. Most preferably, "rapid detection" refers to detecting bacteria in less than 12 hours.

The term "process water" as used herein, is water used in connection with technical plants and production processes. Process water is not considered drinkable and is used to facilitate manufacturing processes.

The term "adenosine triphosphate" (ATP) refers to a molecule used to transport chemical energy within cells. ATP contains adenine, ribose, and three phosphate groups. ATP breaks down into adenosine diphosphate (ADP) and phosphate to release energy.

The term "microorganisms" as used herein, refers to microscopic organisms that are single-celled or multicellular. These organisms may include bacteria, viruses, fungi, and algae.

The term "metabolic activity" as used herein, refers to chemical reactions that occur in living organisms.

The term "bioluminescence" as used herein, refers to the production and emission of light by a living organism. The enzyme luciferase catalyzes the oxidation of luciferin, producing light.

The term "high performance liquid chromatography" (HPLC) as used herein, refers to an analytical chemical technique used to separate, identify, and quantify each component in a mixture.

The term "cation" as used herein, refers to a positively charged ion.

The term "dormant" as used herein, refers to an organism having normal physical functions suspended for a period of time.

The term "colony-forming units" (CFUs) as used herein, refers to an estimate of a number of viable bacterial or fungal cells in a sample. Viable cells are able to multiply under controlled conditions. CFUs are provided as a measure of CFU/mL for liquids or CFU/g for solids.

The term "relative light units" (RLUs) as used herein, refers to an amount of light as measured by a luminometer.

The term "germination conditions" as used herein, refers to conditions favorable for activation, germination, and outgrowth of bacterial spores (endospores).

Detecting the presence of bacteria and bacterial spores is important in many industries. When human health is involved, guidelines dictate the maximum amount of bacteria that may be present. For example, the "Dairyman's Standard" provides requirements for the number of colony-forming units (CFU) of bacteria that may be present per gram of paper or paperboard to be used in dairy products. Samples are cut from the paper or paperboard to be tested and are placed in sealed envelopes. The sample is then cut into small squares and deposited in a sterile blender. Sterile phosphate dilution water is added to the cut-up paper sample in the blender to help disintegrate the sample. Immediately after disintegration, the sample is transferred into one or more petri dishes. Melted agar is poured over the sample in the petri dish and allowed to solidify. Upon solidification, the plates are incubated at 36° C. for 48 hours. After incubation, the plates are examined for the presence and number of CFU with a colony counter.

Industry guidelines limit the number of colony forming units (CFU) present on paper or paperboard products used with dairy products to less than 250 per gram. Some end users may require more or less stringent compliance (<100→1000 CFU/g). In order to comply with spore guidelines for the dairy, food, and healthcare industries, it is important that bacteria that can form spores are detected and properly treated when they are in their most vulnerable, vegetative, state.

Spores are made up of many protective layers that make them resistant to oxidation and chemical attack. Higher biocide doses are needed to kill spores than vegetative cells. It is always more effective to apply biocide to active, vegetative cells. A spore control program must be robust enough to attack cells in the vegetative state and prevent sporulation. Dosages must be high enough to kill vegetative cells before they develop into spores.

One way of detecting microorganisms depends on measuring microbial activity. Microbial activity can be measured using adenosine triphosphate (ATP) concentrations as an indicator of activity. Microbial activity can also be measured using metabolic dyes, including redox dyes (e.g. resazurin and 2-(p-iodophenyl)-3-(p-nitrophenyl) 5-phenyltetrazoliurn chloride (INT)), fluorescent redox dyes (e.g. 5-cyano-2, 3-ditolyl tetrazolium chloride (CTC)) and indicators of enzymatic activity (e.g. carboxyfluorescien diacetate).

Adenosine triphosphate (ATP) measurements have been used for detecting microorganisms in various industries. ATP is used by cells as a source of energy and is an indicator of metabolic activity. ATP can be measured in vegetative bacteria, but bacterial spores contain little to no ATP.

ATP levels are typically measured by a bioluminescence assay involving reactions with luciferase that are quantified with a luminometer. Other methods include colorimetric or fluorometric assays utilizing phosphorylation of glycerol and high performance liquid chromatography (HPLC).

In the method utilizing bioluminescence, luciferase and luciferin from fireflies are mixed with a sample with a cation, such as magnesium, in the presence of oxygen. If ATP is present, it will cause a reaction between luciferase (the substrate) and luciferin (the catalyst) in an oxidation reaction which produces light. Light emissions are detected with a luminometer and reported in relative light units (RLUs). The amount of light produced is proportional to the metabolic activity of microbial organisms present, but does not indicate the number of organisms present. The luciferase/luciferin reaction is well known in the art, and there are commercial sources for the necessary reagents as well as protocols for their use. For example, several luciferase/luciferin reagents along with luciferase are available in commercial kits from, for example, Promega Corp. (Madison, Wis.) and LuminUltra (Fredericton, New Brunswick). Commercially available luciferases include firefly luciferase (*Photinus pyralis*, "Ppy luciferase"). Purified beetle luciferin is also commercially available from Promega.

According to the present disclosure, when spores are placed in nutrient broth containing a germination enhancer and incubated, the spores will germinate into vegetative bacteria. During germination, the ATP production will increase rapidly and measurement of the spike in ATP activity will provide an indication of the presence of spores germinating. Moreover, this process occurs in a relatively short period of time of approximately 5-8 hours into the incubation, depending on the concentration of spores in the sample. Alternatively, samples containing high levels of vegetative cells exhibit high ATP values early in the test protocol; typically within the first hour. ATP in samples may decrease with extended incubation due to the presence of residual biocide. The use of a biocide neutralizing solution may be utilized.

Germination of spores can be observed directly by measuring the initial ATP in a sample before the addition of nutrients and the germination enhancer, and then periodically measuring the ATP during the incubation time of the assay. During this time, vegetative cells produce ATP at steady levels, while spores exhibit a burst of ATP production which can be measured 5-8 hours into the assay, depending on the concentration of spores present in the sample. Spore concentrations in the 100-200 CFU/mL range will produce a burst of ATP between 7 and 8 hours, while high spore concentrations of 1,000-100,000 CFU/mL will exhibit a burst of ATP at around 5 hours.

In some samples, a high level of vegetative bacterial cells may obscure the ATP reading from germinating spores. To mitigate this, an optional 10-15 minute heating step at 80-95° C. may be included at the beginning of the assay. This heating step inactivates vegetative cells, thus eliminating their contribution to ATP levels. Spores, meanwhile, can survive the high temperatures in a dormant state. Upon addition of nutrients and a germination enhancer, spores will then produce a burst of ATP, if present.

To implement this method for the rapid detection of bacterial spores in an industrial process, a sample must first be prepared which will be tested for the presence of bacterial spores. The sample may be collected from any source which could be contaminated with bacterial spores. The sample may be contaminated with bacterial spores, with vegetative bacterial cells, neither, or both. The sample may be taken from a hard surface, a slurry (starch, carbonate, clay, or $TiO_2$), stock fibers, a food or beverage product, a liquid, or packaging or a paper board product sample.

Non-limiting examples of facilities having hard surfaces include food and beverage plants, dairy plants, farms and dairies, breweries, ethanol plants, full service and quick service restaurants, grocery stores, warehouse and retail stores, commercial or office space, hotels, motels, hospitals, paper mills, industrial manufacturing plants including automotive plants, cooling towers, water treatment plants, refineries, oil and gas fields and pipelines, and drilling platforms. Examples of hard surfaces include food and beverage processing equipment including pipes, tanks, evaporators, spray nozzles and the like, dairy processing equipment, milk tanks, milk trucks, milking equipment, countertops, cooking surfaces, bathroom surfaces such as sinks and toilet handles, light switch panels, doorknobs, call buttons, phone handles, remote controls, desktops, patient rails, grab bars, surgical instruments, equipment inside paper mills including pipes, chests, headboxes, broke towers, saveall blades, forming wire, and the like.

Samples on hard surfaces may be taken with a sterile swab or other sterile device that can be used to collect microorganisms from a hard surface, such as: medical tape, cotton cloth, cellulose cloth, and the like. If the surface is dry, a solvent may be applied with a swab to dissolve any bacterial residue that may be present and suspend the residue in the solvent for testing. Examples of solvents can include, but are not limited to: sterile water, sterile phosphate buffer, sterile Tris EDTA (TE) buffer, a dilute detergent solution such as TWEEN, and the like.

Non-limiting examples of liquids include process waters, incoming water, cooling tower water, treated and untreated wastewater, paper furnish (thin and thick stock), white water, uhle box water, tray water, fruit and vegetable flume water, protein (e.g., poultry, pork, red meat, seafood) process water, hydroponic waters or seafood farming water, water for agricultural uses. Samples of liquids may be aliquoted into sterile containers from the source of potential contamination.

Non-limiting examples of food and beverage products include milk, beer, wine, drinking water, fruits and vegetables, protein such as poultry, pork, red meat or seafood, ready-to-eat meat, cheese, prepared foods, frozen foods, ice cream.

Non-limiting examples of packaging and products include: paper products such as finished paper products and finished board products both for food contact and non-food contact grades; drapes for surgical or medical use; aseptic packaging containers; plastic food and beverage containers (e.g., yogurt containers, milk containers, deli containers); food cans (e.g., soup cans); aluminum or PET beverage containers; bags or films or modified atmosphere packaging. The products can be tested before they leave the manufacturing facility, for example, at the paper mill, or at the point of use such as at the food or beverage plant. Samples of paper products may be tested according to the procedure described in the Dairyman's Standard (TAPPI Test Method T449 Bacteriological Examination of Paper and Paperboard, or ISO8784 Pulp and Board Microbiological Examination).

According to some embodiments, an optional initial ATP measurement is taken of the sample. As described above, the sample may be combined with luciferase and luciferin along with a cation, oxygen and tris buffer or similar. Light produced by the reaction is measured in relative light units (RLUs). The measurement may be taken with a luminometer. Alternatively, the initial ATP measurement may be taken by HPLC. In some embodiments, the vegetative cells may be inactivated with an optional heating step. Vegetative cells may be inactivated by heating the sample for about 5 to about 15 minutes, about 7 to about 13 minutes or about 9 to about 11 minutes. The cells may be heated at a temperature of about 80° C. to about 110° C., about 85° C. to about 105° C. or about 90° C. to about 100° C. Preferably, the sample is heated for 10 minutes at a temperature of about 95° C. Heating a sample at 80° C. is the accepted method to eliminate vegetative cells from a sample, however, laboratory testing revealed that some vegetative cells survive this level of heat.

In some embodiments, the sample is incubated in conditions that initiate germination of bacterial spores. This generally involves at least providing nutrients and proper temperature conditions to the spores. A nutrient broth including an optional germination enhancer may be added to a sample and incubated at a temperature of about 30° C. to about 45° C., about 35° C. to about 40° C., or about 36° C. to about 38° C. to effectively initiate germination of spores. Examples of commercially available nutrient broths include nutrient broth, trypticase soy broth, lysogeny broth, Luria broth, beef extract broth, and terrific broth. Effective germination enhancers include L-alanine, inosine, glucose, amino acids, and potassium bromide. Preferably, the germination enhancer is L-alanine. In one embodiment, the sample is incubated at 37° C. to induce germination of spores.

ATP levels are monitored over time, by taking ATP readings at specified time intervals, as the sample is incubating. Light emissions are measured with a luminometer at intervals throughout the incubation period. New samples are taken at each time interval and combined with ATP reagents to produce each luminescence reading. ATP measurements may be taken every 2 hours, every 1 hour, every 30 minutes, every 15 minutes, or every 5 minutes. Preferably, ATP measurements are taken at least every hour over a 5-8 hour period. Alternatively, HPLC may be utilized to measure ATP levels in the sample. HPLC measurements may also be taken at least every hour to monitor ATP levels. The same procedure may be conducted using dyes to detect microbial activity based on redox changes or metabolic activity. Samples can be examined for visual evidence of a color change, spectrophotometrically or by measuring fluorescence.

As was discussed above, when spores germinate, they produce a burst of ATP due to the increase in metabolic activity. This burst of ATP production may be observed at different points in the incubation period depending on the concentration of spores present, but will typically appear between 5 and 8 hours after incubation begins. Spore concentrations in the 100-200 CFU/mL (colony forming units per milliliter) range will produce a burst of ATP between 7 and 8 hours, while high spores concentrations of 1,000-100,000 CFU/mL will exhibit a signal at around 5 hours. If vegetative cells are present in the sample (and were not heat inactivated), a steady level of ATP production will be detected throughout the incubation period. Typical measurements for vegetative cells may be in the range of about 5,000-200,000 RLUs. However, the germination of bacterial spores will exhibit a much higher amount of ATP, measuring at least 500 times higher RLU than the initial measurement. Typical bursts of ATP may be measured in the range of 10 to 500 times higher RLUs than initial measurement, depending on the concentration of spores present in the sample. Thus, the presence of an ATP burst indicates that spores are in the sample, while an absence of an ATP burst shows that spores are not in the sample. If no ATP is measured in the sample, then no microorganisms are present at all.

Once it has been determined that spores are present in the sample, an antimicrobial treatment is selected. If spores are detected, treatments may be selected from the following: hypochlorite, chlorine dioxide, ozone, glutaraldehyde, sodium hypochlorite, monochloramine, peroxyacetic acid, 2,2-dibromo-3-nitrilopropionamide (DBNPA), 5,5-dimethylhydantoin (DMH), alcohols, peracids, and combinations thereof.

In a paper mill, sodium hypochlorite (bleach) is effective in process and water systems between pH 6.0 and 7.5 and requires at least 20 minutes of contact time. In the effective pH range, most of the chlorine is present as HOCl which is easily consumed by oxidant demand. In high demand systems high doses may need to be applied to achieve the desired target residual. Free chlorine can be effective against spores when dosed to achieve a target residual between 0.4 and 0.5 ppm. Residual free chlorine above 0.5 ppm can negatively affect machine efficiency because it oxidizes dyes, OBAs, felts and machine surfaces. Therefore, good control of the stock system is recommended to minimize residual needed on the wet end. Sodium hypochlorite can be applied continuously to a blend chest. For broke tanks, the sodium hypochlorite must be applied in combination with a non-oxidizing biocide such as glutaraldehyde.

Chlorine dioxide is also effective in paper mills in systems from pH 5 to 10 and is less likely to be consumed by oxidant demand than bleach. Furthermore, chlorine dioxide does not contribute to the formation of AOX (adsorbable organic halides, i.e.; chlorophenols, dioxin) as chlorine does. This makes it a suitable alternative where local regulations limit the use of chlorine. Delivered as a gas dissolved in water, chlorine dioxide is prone to rapid volatilization when exposed to the open air. Feed points must be considered carefully to avoid volatilization. A large blend chest or white water storage chest with good mixing is an ideal feed point for $ClO_2$. As with bleach, good control of the stock system will minimize treatment needed on the wet end and improve machine compatibility. When chlorine dioxide is used as the backbone of the spore control program, broke tanks are best treated with non-oxidizing biocide such as glutaraldehyde.

Monochloramine (MCA) (where available and registered as a biocide) is effective in systems from pH 7 to 9 and is less likely to be consumed by oxidant demand than bleach. MCA is produced by mixing an ammonia source with chlorine under controlled conditions. This is commonly done with on-site generation by reacting diluted sodium hypochlorite with ammonium sulfate solution at a pH of 9-10 to create a final MCA concentration of 3,000 to 6,000 ppm. MCA is not a good sporicide, but it can be extremely effective at controlling a broad spectrum of bacteria including spore-forming bacteria in the vegetative state. The key is to maintain consistent biocontrol in the stock systems and incoming water. MCA does not respond quickly to process upsets, and therefore supplemental glutaraldehyde is recommended. In a paper mill, stock chests with good mixing are ideal feed points for MCA. MCA can be fed to the white water but, residual concentrations should be maintained between 2-3 ppm to minimize corrosion potential. Good control of the stock system and incoming water will minimize treatment needed on the wet end and improve machine compatibility.

Peracetic acid is delivered as a solution of peracetic acid (PAA), hydrogen peroxide and acetic acid at equilibrium. While high doses of $H_2O_2$ are effective at killing spores, in an equilibrium solution, PAA is considered the main active ingredient. PAA will not contribute to the formation of AOX and can be used where local regulations limit the use of chlorine. PAA is most effective in systems from pH 5-7, higher doses may be required to achieve efficacy above pH 7. Although it is considered a strong oxidant, PAA may take a longer contact time than bleach or $ClO_2$ and requires higher doses. PAA can be used in combination with $ClO_2$ but can neutralize a hypochlorite program. PAA and hypochlorite can only be used to treat the same machine if feed points are considered carefully to avoid mixing the two. PAA is most effective when complimented with DBNPA (2, 2 dibromo-3-nitrilopropionamide) in the same process steams. Target concentrations for PAA are 5.0 ppm for 1 hour of contact time or 15 ppm for 20 to 60 minutes of contact time.

Chlorine is stabilized with a non-biocidal precursor chemistry such as dimethyl hydantoin, urea, sulfamic acid, sodium sulfamate, ammonium carbamate, ammonium sulfate, ammonium chloride, and ammonium bromide. The balance between persistence and quick-kill at 4:1 $Cl_2$:DMH (5,5-dimethylhydantoin) is recommended for spore control with DMH-stabilized chlorine.

Often, a non-oxidant is needed as a supplement to an oxidant program. Glutaraldehyde affects both vegetative cells of spore-forming bacteria and bacterial spores. It is effective in systems within a pH range from 6.0 to 9.0.

Non-chemical treatments like extreme heat and UV radiation can also be used. Targeting spore-forming bacteria when they are in their vegetative state expands the list of effective biocides to include DBNPA, isothiazolin, quaternary amines, and the like. Once an appropriate treatment has been selected, it is applied to the part of the process where spore-forming bacteria are present in a vegetative state when no spores are detected. This could include a hard surface, food or beverage product, liquid, package, or paper product at the point in production where the contamination has been detected. Because the method takes no longer than 8 hours to complete, the bacterial contamination can be eliminated quickly to prevent spore formation downstream. Additionally, the treatment can be done while equipment is offline for cleaning or without quarantining product for multiple shifts and production problems can be corrected more quickly. After the application of treatment, a subsequent round of testing should take place to ensure elimination of spores has taken place. The ability to act with the correct chemical in the correct place in production results in both cost and time savings.

For a more complete understanding of the disclosure, the following examples are given to illustrate some embodiments. These examples and experiments are to be understood as illustrative and not limiting. All parts are by weight, except where it is contrarily indicated.

EXAMPLES

Example 1: Comparison of ATP Production in a Mixed Population of Vegetative Cells and Spores Under Various Conditions A LuminUltra QuenchGone21 Industrial ATP Kit was used to measure ATP levels in samples containing a mixture of vegetative cells and spores. An industrial water sample from a paper mill was determined to have a mixture of vegetative cells and bacteria. Confirmation and quantification of both bacterial forms was determined with plating on R2A agar. ATP production was measured over the course of 6 hours under various conditions.

Figure 2:
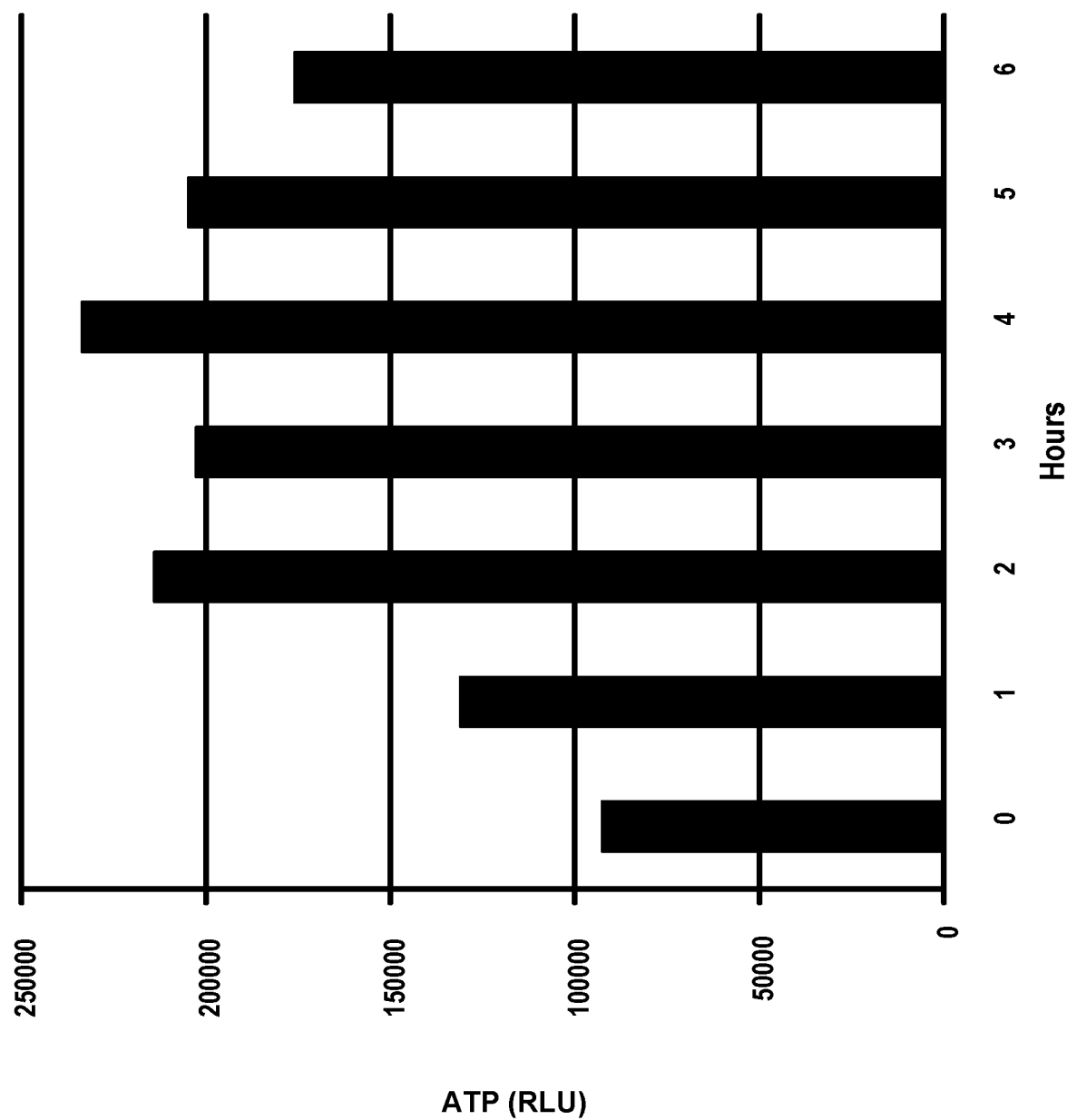
FIG. 2 is a chart of ATP production over time in an industrial water sample without heat treatment, with germination enhancer, and without nutrients.
Figure 3:
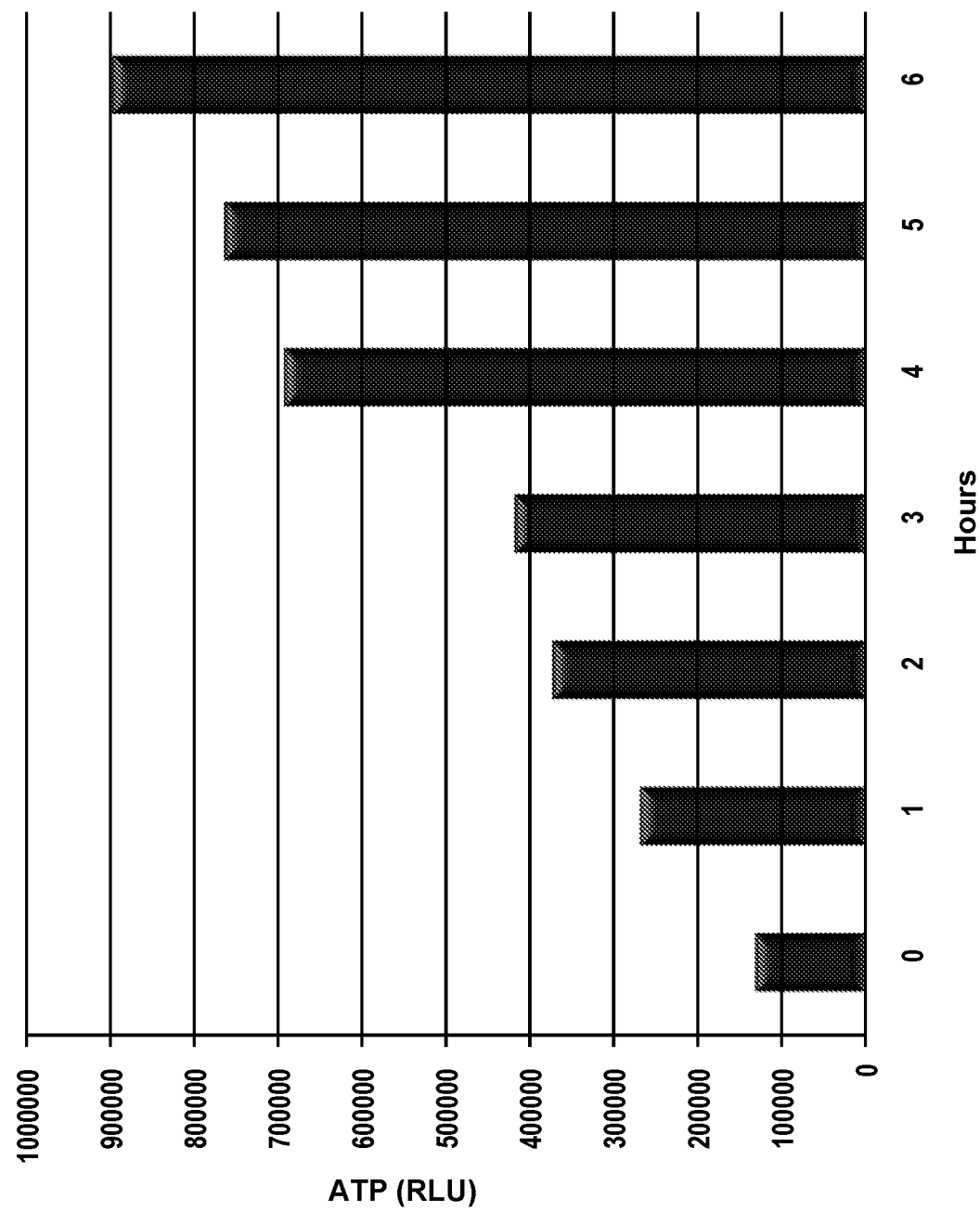
FIG. 3 is a chart of ATP production over time in an industrial water sample without heat treatment, with germination enhancer, and with nutrients.
Figure 4A:
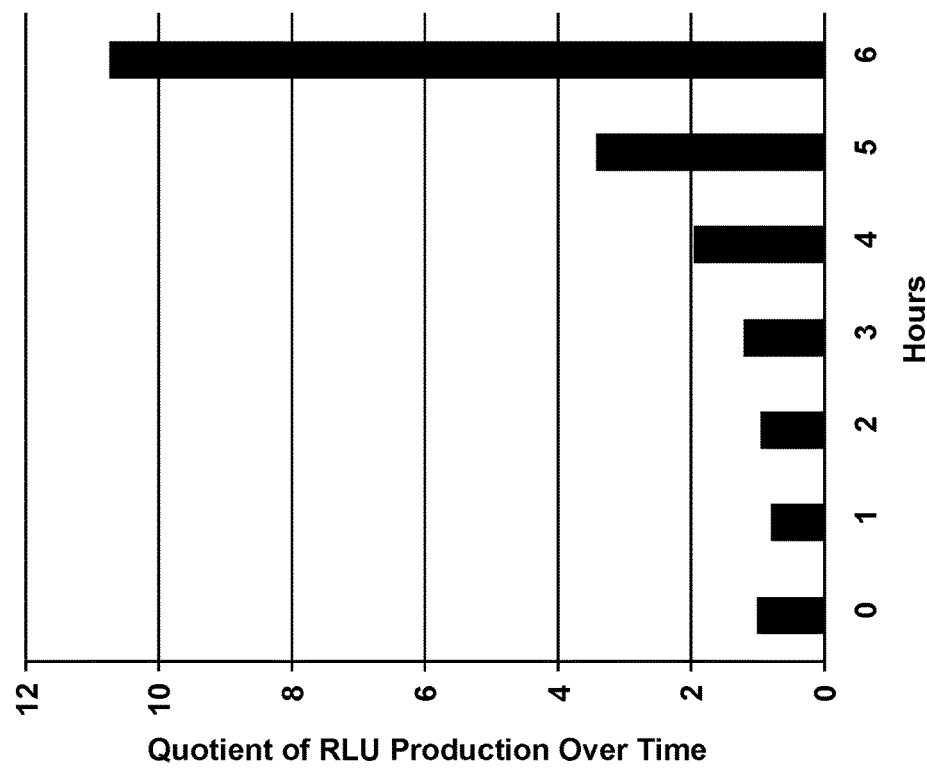
FIG. 4A is a chart of ATP production (represented in RLUs) over time in an industrial water sample with heat treatment, with germination enhancer, and with nutrients.
Figure 4B:
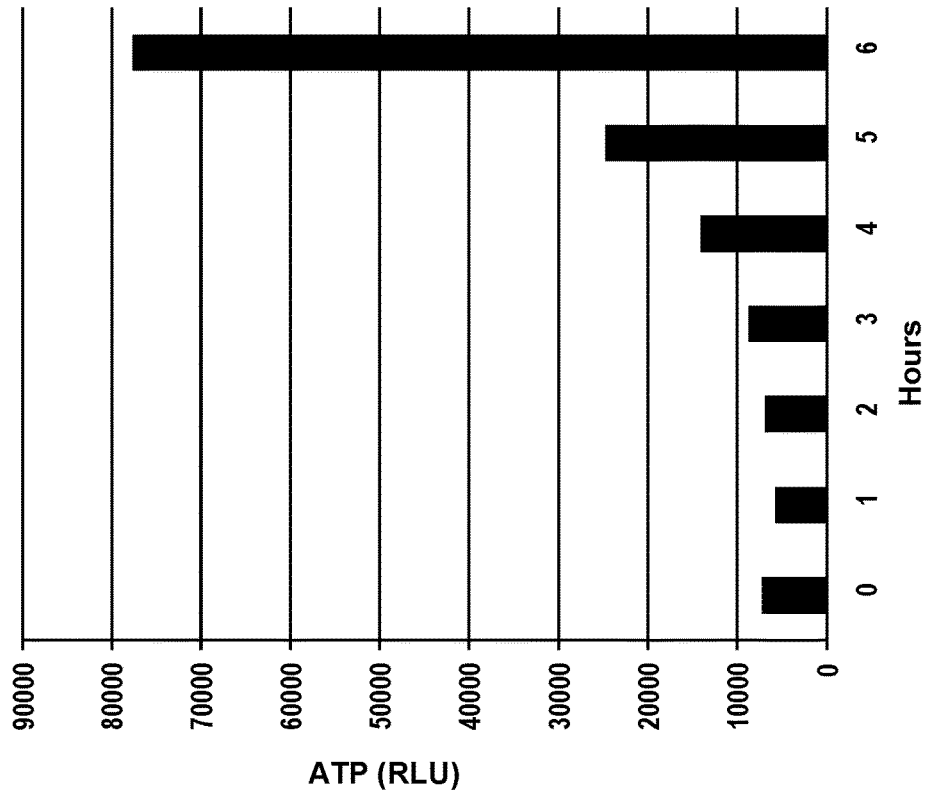
FIG. 4B is a chart of ATP production (represented in quotient of RLU production over time) in an industrial water sample with heat treatment, with germination enhancer, and with nutrients.

In the absence of a heating step to eliminate vegetative bacteria, a germination enhancer, and nutrients, the ATP production time course looked like that in FIG. 1. In the absence of a heating step and nutrients, but in the presence of a germination enhancer the ATP production time course looked like that in FIG. 2. In the presence of both the germination enhancer and nutrients, but in the absence of a heating step the ATP production time course looked like that in FIG. 3. In the presence of nutrients and a germination enhancer the production of ATP steadily increased over the course of 6 hours. When a heating step was included prior to addition of the germination enhancer and nutrients, the ATP production time course looked like that in FIGS. 4A (RLUs) and 4B (quotient of RLU production over time).

The ATP production by the vegetative cells was removed by heat inactivation, and only the ATP produced by spores was observed. Addition of nutrients and a germination enhancer accelerates the germination of spores and also production of ATP in vegetative cells. A heat inactivation step is necessary to eliminate production of ATP by vegetative cells in order to be able to detect ATP generated by germinating spores. Plotting data as quotient of RLU production over time allows for easy comparison of multiple samples.

Example 2: Spore Detection in Process Water Samples

Figure 5:
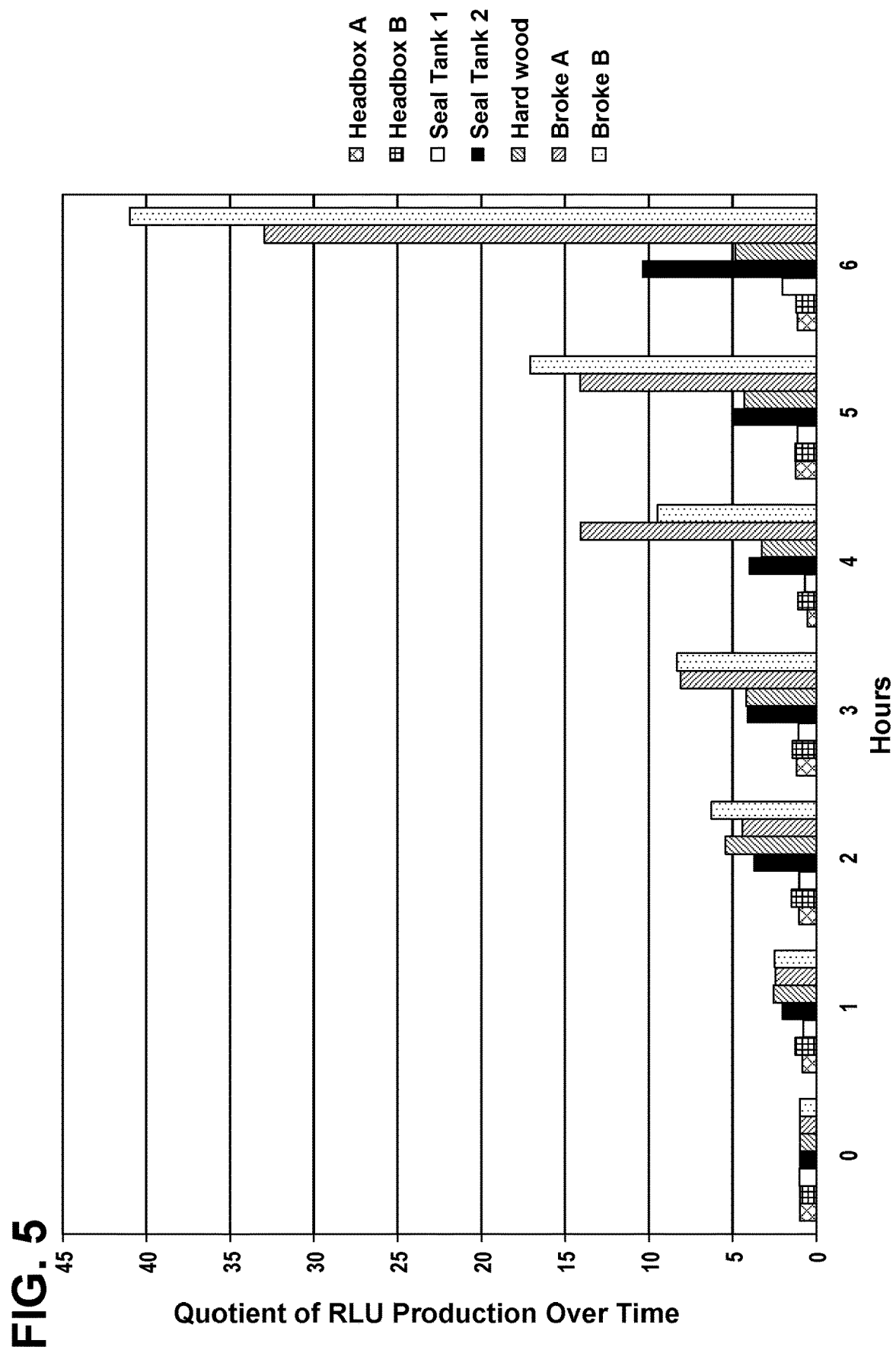
FIG. 5 is a ATP production time course chart of 7 industrial water samples treated with heat, germination enhancers, and nutrients.

Seven process water samples were collected from a papermill with two paper machines. Each sample had an unknown amount of vegetative cells and spores. Samples were heat treated prior to addition of nutrients and a germination enhancer. ATP production was measured hourly over the course of 6 hours using the LuminUltra QuenchGone21 Industrial ATP Kit (FIG. 5).

It was determined that spores were present in three out of the seven samples: seal tank 2, broke A and broke B. Brokes A and B had the highest levels of spores based on signal intensity at 6 hours relative to t=0. The seal tank had significantly less spores than brokes A and B. In order to remediate spores in this process, it was determined that the most effective biocide addition points were the two broke towers.

The above specification, examples and data provide a complete description of the manufacture and use of the composition. Since many embodiments can be made without departing from the spirit and scope of the disclosure, the invention resides in the claims.

What is claimed is:

1. A method of differentiating and treating bacterial spores and vegetative cells in an industrial system comprising:
   preparing a sample from an industrial system to be tested for the presence of bacterial spores;
   measuring a baseline level of microbial metabolic activity in the sample;
   incubating the sample in conditions to initiate germination;
   monitoring subsequent levels of microbial metabolic activity in the sample;
   detecting the presence or absence of a burst of microbial metabolic activity in the sample after about 5 to 8 hours of incubation;
   selecting an antimicrobial treatment based upon the presence or absence of spores, vegetative cells, or both spores and vegetative cells; and
   applying the antimicrobial treatment to the industrial system.

2. The method of claim 1, wherein microbial metabolic activity is determined by measuring adenosine triphosphate (ATP).

3. The method of claim 1, wherein microbial metabolic activity is detected by metabolic dyes.

4. The method of claim 1, wherein the sample contains an unknown quantity of spores, vegetative cells, or both spores and vegetative cells; and wherein the preparing comprises:
   collecting the sample;
   disintegrating the sample, if solid; and
   placing the sample in a dish or container.

5. The method of claim 1, wherein the sample is collected from a hard surface, a liquid, a slurry, or a paper product.

6. The method of claim 5, wherein the hard surface is selected from the group consisting of food and beverage processing equipment, pipes, tanks, evaporators, spray nozzles, dairy processing equipment, milk tanks, milk trucks, milking equipment, countertops, cooking surfaces, sinks, toilets, light switch panels, doorknobs, call buttons, phone handles, remote controls, desktops, patient rails, grab bars, surgical instruments, chests, headboxes, broke towers, saveall blades, and forming wire.

7. The method of claim 5, wherein the liquid is selected from the group consisting of process waters, incoming water, cooling tower water, treated and untreated wastewater, paper furnish, thin and tick stock, white water, uhle box water, tray water, fruit and vegetable flume water, protein process water, hydroponic waters or seafood farming water, and water for agricultural uses.

8. The method of claim 5, wherein the paper product is selected from the group consisting of finished paper products, finished board products, food-contact grade paper, non-food-contact grade paper, drapes for surgical or medical use, aseptic packaging containers, plastic food containers, plastic beverage containers, food cans, aluminum and PET beverage containers, bags, films, and modified atmosphere packaging.

9. The method of claim 2, wherein the measuring comprises:
adding luciferase and luciferin to the sample; and
measuring light emissions in relative light units (RLUs).

10. The method of claim 1, wherein the incubating comprises:
providing a nutrient broth and a germination enhancer to the sample;
optionally adding a biocide neutralizing agent; and
incubating the sample at a temperature of about 30° C. to about 45° C.

11. The method of claim 10, wherein the nutrient broth is 2× nutrient broth and the germination enhancer is L-alanine.

12. The method of claim 2, wherein the measuring comprises adding luciferase and luciferin to the sample and measuring light emissions at multiple points of time during an 8-hour period of incubation.

13. The method of claim 12, wherein the measuring occurs every hour.

14. The method of claim 2, wherein the measuring comprises measuring ATP levels by H PLC.

15. The method of claim 1, wherein the burst of microbial metabolic activity comprises measuring at least 10 times higher microbial metabolic activity than in the initial measurement in the sample, and determining that spores are present in the sample.

16. The method of claim 1, further comprising inactivating vegetative cells in the sample after the step of measuring the baseline level of microbial metabolic activity.

17. The method of claim 16, wherein the inactivating comprises heating the sample for about 5 to 15 minutes at a temperature of about 80° C. to about 110° C.

18. The method of claim 1, wherein, if spores are present in the sample, the antimicrobial treatment is selected from the group consisting of chlorine dioxide, ozone, glutaraldehyde, sodium hypochlorite, peracid, UV, extreme heat, and radiation.

19. The method of claim 1, wherein, if vegetative cells are resent in the sample, the antimicrobial treatment is selected from the group consisting of: isothiazolin; glutaraldehyde; dibromonitrilopropionamide; carbamate; quaternary ammonium compounds; sodium hypochlorite; chlorine dioxide; peracetic acid; ozone; chloramines; bromo-sulfamate; bromo-chloro-dimethyl hydantoin; dichloro-dimethyl hydantoin; monochloramine; sodium hypochlorite used in combination with ammonium salts and stabilizers; and a combination thereof.

20. The method of claim 5, wherein applying the antimicrobial treatment to the industrial system comprises applying the antimicrobial treatment to the hard surface, liquid, slurry, or paper product.

21. The method of claim 1, wherein the presence or absence of bacterial spores in the sample is determined within 8 hours of preparing the sample, and spores are differentiated from vegetative cells.

\* \* \* \* \*